US007122684B2

(12) United States Patent
Brown et al.

(10) Patent No.: US 7,122,684 B2
(45) Date of Patent: Oct. 17, 2006

(54) PROCESS FOR PREPARING 1,2-DIAMINO COMPOUNDS

(75) Inventors: Jack D. Brown, Moseley, VA (US); Peter J. Harrington, Louisville, CO (US); Robert C. Hughes, Grand Haven, MI (US)

(73) Assignee: Roche Colorado Corporation, Boulder, CO (US)

( * ) Notice: Subject to any disclaimer, the term of this patent is extended or adjusted under 35 U.S.C. 154(b) by 29 days.

(21) Appl. No.: 10/388,064

(22) Filed: Mar. 13, 2003

(65) Prior Publication Data

US 2004/0180933 A1 Sep. 16, 2004

(51) Int. Cl.
C07D 203/26 (2006.01)
C07D 209/56 (2006.01)
C07D 209/38 (2006.01)
C07C 69/74 (2006.01)
C07C 213/00 (2006.01)

(52) U.S. Cl. .................. 548/961; 549/437; 549/513; 560/126; 564/475

(58) Field of Classification Search ............... 548/961; 549/513, 437; 560/126; 564/475
See application file for complete search history.

(56) References Cited

U.S. PATENT DOCUMENTS

| | | | |
|---|---|---|---|
| 5,763,483 A | 6/1998 | Bischofberger et al. | |
| 5,859,284 A | 1/1999 | Kent et al. | |
| 5,866,601 A | 2/1999 | Lew et al. | |
| 5,886,213 A | 3/1999 | Kent et al. | |
| 5,952,375 A | 9/1999 | Bischofberger et al. | |
| 5,994,377 A | 11/1999 | Kim et al. | |
| 6,057,459 A | 5/2000 | Kent et al. | |
| 6,225,341 B1 * | 5/2001 | Bischofberger et al. | 514/459 |
| 6,403,824 B1 | 6/2002 | Abrecht et al. | |
| 6,437,171 B1 * | 8/2002 | Karpf et al. | 560/125 |
| 6,518,438 B1 * | 2/2003 | Kent et al. | 548/961 |
| 2002/0095040 A1 | 7/2002 | Karpf et al. | |

FOREIGN PATENT DOCUMENTS

| | | |
|---|---|---|
| EP | 1059283 | 12/2000 |
| EP | 1 146 036 A2 | 10/2001 |
| FR | 1.559.511 | 3/1969 |
| WO | WO 96/26933 | 9/1996 |
| WO | WO 98/07685 | 2/1998 |
| WO | WO 99/14185 | 3/1999 |
| WO | WO 01/28981 | 4/2001 |

OTHER PUBLICATIONS

Weissberger, Heterocyclic compoounds with three and four membered rings Part One, Interscience publishers, (1964), pp. 316,552,555.*
C. U. Kim, et al., "Influenza Neuraminidase Inhibitors Possessing a Novel Hydrophobic Interaction in the Enzyme Active Site: Design, Synthesis, and Structural Analysis of Carbocyclic Sialic Acid Analogues with Potent Anti-Influenza Activity," *J. Am. Chem. Soc.*, 119, 681-690 (1997).
J. C. Rohloff, et al., "Practical Total Synthesis of the Anti-Influenza Drug GS-4104," *J. Org. Chem.*, 63, 4545-4550 (1998).
M. Chini, et al., "Lanthanide (III) Triflouromethanesulfonates as Extraordinarily Effective New Catalysts for the Aminolysis of 1,2-Epoxides," *Tetrahedron Lett.*, 35, 433-436 (1994).
P. Van de Weghe, et al., "Ring Opening Reactions of Epoxides Catalyzed by Samarium Iodides," *Tetrahedron Lett.*, 36, 1649-1652 (1995).
Y. Yamamoto, et al., "Regio- and Stereo-selective Ring Opening of Epoxides with Amide Cuprate Reagents," *J. Chem. Soc., Chem. Commun.*, 1201-1203 (1993).
M. Caron, et al., "Ti(O-i-Pr)$_4$-Medicated Nucleophilic Openings of 2,3-Epoxy Alcohols. A Mild Procedure for Regioselective Ring-Opening." *J. Org. Chem.*, 1 50, 1557-1560 (1985).
M. Muller, et al., "Synthesis of (−)-3-Amino-3-deoxyquinic Acid," *J. Org. Chem.*, 63, 9753-9755 (1998).
G.E. McCasland, et al., "Stereochemistry of Aminocyclanols. Synthesis of *cis* Epimers via Oxazolines. The 2-Aminocyclopentanois," *J. Am. Chem. Soc. 72*, 2190-2195 (1950).
P.B. Talukdar, et al., "Chemistry of Ethylenimine. V. Cycloheptenimine or 8-Azabicyclo[5.1.0]octane," *J. Org. Chem.* 24, 555-556 (1959).
S.P. McManus, et al.; "The Synthesis of Aminoalcohols From Epoxides And Amonia," *Syntheic Communications 3*, 177-180 (1973).

(Continued)

*Primary Examiner*—Thomas McKenzie
*Assistant Examiner*—Raymond Covington
(74) *Attorney, Agent, or Firm*—Lathrop & Gage LC

(57) ABSTRACT

The invention provides a multi-step process for preparing 1,2-diamino compounds of formula

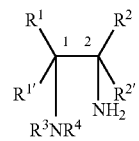

I wherein $R^1$, $R^{1'}$, $R^2$, $R^{2'}$, $R^3$ and $R^4$ have the meaning given in the specification and pharmaceutically acceptable addition salts thereof, from 1,2-epoxides of formula

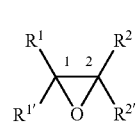

II wherein $R^1$, $R^{1'}$, $R^2$ and $R^{2'}$ have the meaning given in the specification.

47 Claims, No Drawings

OTHER PUBLICATIONS

M. Mousseron, et al., "No. 173.—Recherches en serie alicyclique (34° memoire)," *Bull. Soc. Chim. Fr.* 757-766 (1952).

P. Barbaro, et al., "New Enantiomerically Pure Aminoalcohols from (R)-α-Methylbenzylamine and Cyclohexene Oxide," *Tetrahedron: Asymmetry* 7, 843-850 (1996).

J.A. Deyrup, et al. "1,2,3-Oxathiazolidines—a New Heterocyclic System," *J. Org. Chem.* 34, 175-179 (1969).

M. Yoshida, et al., "Selective Synthesis of Five and Six Membered Cyclic Carbamates by the Reaction of 2-(1-Haloalkyl)Oxiranes with Carbon Dioxide and Aliphatic Primary Amines," *Heterocycles*, 35, 623-626 (1993).

S. Zhao, et al., "Regioselective and Stereoselective Syntheses of 1,2,3-Triaminocyclohexane Derivatives," *J. Org. Chem.* 58, 4043-4048 (1993).

M. Meguro, et al., "Ytterbium Triflate and High Pressure-mediated Ring Opening of Epoxides with Amines," *J. Chem. Soc., Perkin Trans. 1*, 2597-2601 (1994).

G.H. Posner, et al., "Organic Reactions at Alumina Surfaces. Mild and Selective Opening of Epoxides by Alcohols, Thiols, Benzeneselenol, Amines, and Acetic Acid," *J. Am. Chem. Soc.* 99, 8208-8214 (1977).

G.H. Posner, et al., "Organic Reactions at Alumina Surfaces. Mild and Selective Opening of Arene and Related Oxides by Weak Oxygen and Nitrogen Nucleophiles," *J. Am. Chem. Soc.* 99, 8214-8218 (1977).

G.H. Posner, "Organic Reactions at Alumina Surfaces," *Angew. Chem. Int. ed. Engl.* 17, 487-496 (1978).

J. M. Chong, et al., "Nucleophilic Openings of 2,3-Epoxy Acids and Amides Mediated by $Ti(O-i-Pr)_4$ Reliable C-3 Selectivity," *J. Org. Chem.* 50, 1560-1563 (1985).

S.Y. Ko, et al., "In Situ Opening of Epoxy Alcohols: A Convenient Alternative to the Isolation of Unstable Epoxy Alcohols," *J. Org. Chem.* 51, 5413-5415 (1986).

M. Canas, et al., "Regioselective Ring Opening of Chiral Epoxyalcohols by Primary Amines," *Tetrahedron Lett.* 32, 6931-6934 (1991).

H. Urabe, et al., "Ring Opening of the Epoxide Moiety of (2S, 3S, 4S)-4-Amino-2,3-epozy-1-alkanol and Its Derivatives: A Key Role of $Ti(O-i-Pr)_4$ as a Mild Catalyst," *Tetrahedron* 48, 5639-5646 (1992).

S. Sagawa, et al., "Catalytic Asymmetric Aminolysis of 3,5,8-Trioxabicyclo[5.1.0]oxtane Providing an Optically Pure 2-Amino-1,3,4-butanetriol Equivalent," *J. Org. Chem.* 64, 4962-4965.(1999).

M. Fujiwara, et al., "Tetraphenylstibonium Triflate as a Regio- and Chekmoselective Catalyst in the Reaction of Oxiranes with Amines," *Tetrahedron Lett.*, 30, 739-742 (1989).

M. Chini, et al., "Metal Salts as New Catalysts for Mild and Efficient Aminolysis of Oxiranes," *Tetrahedron Lett.*, 31, 4661-4664 (1990).

M. Chini; et al., "Regioalternating Selectivity in the Metal Salt Catalyzed Aminolysis of Styrene Oxide," *J. Org. Chem.* 56, 5939-5942 (1991).

C. Anaya de Parrodi, et al., "Synthesis of Enantiomerically Pure N-(S)-α-Methylbenzyl-β-Aminoalcohols by Regio- and Stereoselective Ring Opening of Epoxides," *An. Quim. Int. Ed.*, 92, 400-404 (1996).

M. Beaton, et al. "Synthesis of 6-Amino-3,5-deoxyinositol 1-Phosphates via (1R,2R,4R,6S)-1,6-Epoxy-2,4-*bis*-benzyloxycyclohexane Aminolysis in Aqueous Ytterbium Triflate Solution," *Tetrahedron Lett.*, 39, 8549-8552 (1998).

J. Auge, et al., "Lithium Trifluoromethanesulfonate-catalysed Aminolysis of Oxiranes," *Tetrahedron Lett.*, 37, 7715-7716 (1996).

K.G. Akamanchi, et al., "Diisopropoxyaluminium Trifluoroacetate: A New Off the Shelf Metal Alkoxide Type Reducing Agent for Reduction of Aldehydes and Ketones," *Synlett.* 371-372 (1997).

S. Rampalli, et al., "Diisopropoxyaluminium Trifluoroacetate: A New Promoter for Aminolysis of Epoxides," *Synthesis*, 1, 78-80 (2000).

G.S. Kauffman, et al., "An Efficient Chiral Moderator Prepared from Inexpensive (+)-3-Carene: Synthesis of the HIV-1 Non-Nucleoside Reverse Transcriptase Inhibitor DPC 963," *Org. Lett.*, 2, 3119-3121 (2000).

M. Karpf, et al., "New, Azide-Free Transformation of Epoxides into 1,2-Diamino Compounds: Synthesis of the Anti-Influenza Neuraminidase Inhibitor Oseltamivir Phosphate (Tamiflu)," *J. Org. Chem.* 66, 2044-2051 (2001).

G.E. Coates, et al., "Some 1-Butylmagnesium and Related Complexes. Reactions between Hydrides and Organomagnesium Compounds," *J. Chem. Soc. (A)* 514-418 (1968).

D.F. Evans, et al., "Studies in Grignard Reagents. Part II. $NNN^1N^1$-Tetraethylethylene-diamine Grignard Adducts," *J. Chem. Soc. (A)*, 1648-1649 (1967).

J-Y. Ham, et al., "A New Convenient Method for the Monoprotection of αω-alkanediamines," *Bull. Korean Chem. Soc.*, 15, 1025-1027 (1994).

Y. Ueda, et al.; "Highly Regioselective Formation of Bromohydrins by Reaction of Epoxy-Azetidinones with $MgBr_2$: An Alternative Route to 4-Bromomethylcarbonylmethyl-2-Azetidinone, A Key Carbapenem Precursor," *Tetrahedron Lett.*, 29, 5197-5200 (1988).

K. Nakajima, et al., "Studies on Aziridine-2-carboxylic Acid. I. Synthesis of the Optically Active $_L$-Aziridine-2-carboxylic Acid and Its Derivatives," *Bull. Chem. Soc. Jpn.*, 51, 1577-1578 (1978).

M. Poch, et al.; "A Versatile Enantiospecific Approach to 3-Azetidinols and Aziridines," *Tetrahedron Lett.*, 32, 6935-6938 (1991).

C. Anaya de Parrodi, et al.; "Application of Phosphorylated Reagents Derived from N,N´-di-[S]-α-phenylethyl]-cyclohexane-1,2-diamines in the Determination of the Enantiomeric Purity of Chiral Alcohols," *Tetrahedron: Asymmetry*, 9, 2093-2099 (1998).

F. Winternitz, et al.; "No. 70.—Queiques Nouvelles Reactions de la Cyclohexenimine-1,2," *Bull. Soc. Chim.,Fr.* 382-391 (1955).

J. Szmuszkovicz, et al.; "Benzeneacetamide Amines: Structurally Novel Non-mµ Opioids," *J. Med. Chem.*, 25, 1125-1126 (1982).

D.C. Rees.; "Synthesis of Perhydro-2(1H)-quinoxalinones and Perhydropyrrolo[1,2-α]quinoxalin-4(5H)-one Derivatives," *J. Het. Chem.*, 24, 1297-1300 (1987).

C.R. Clark, et al.; "Highly Selective $_K$ Opioid Analgesics. Synthesis and Structure-Activity Relationships of Novel N-[2-Aminocyclohexyl)aryl]acetamide and N-[2-Aminocyclohexyl)aryloxy]acetamide Derivatives," *J. Med. Chem.*, 31, 831-836 (1988).

P.R. Halfpenny, et al., "Highly Selective $_K$ Opioid Analgesics. 2. Synthesis and Structure-Activity Relationships of Novel N-[2-Aminocyclohexyl)aryl]acetamide Derivatives," *J. Med. Chem.* 32, 1620-1626 (1989).

D.C. Rees; "Nucleophilic Addition of 2-, 3-, or 4-[2-(Methylamino)ethyl]pyridine to the Aziridine, 7-Methyl-7-azabicyclo[4.1.0]heptane," *J. Heterocycl. Chem.*, 27, 147-150 (1990).

M. Meguro, et al.; "Ytterblum Triflate Catalyzed Ring Opening of Aziridines with Amines," *Tetrahedron Lett.*, 35, 7395-7398 (1994).

G. Hofle. et al.; "4-Dialkylaminopyridines as Highly Active Acylation Catalysts," *Angew Chem. Int. Ed. Engl.*, 17, 569-583 (1978).

S. Leppanen, et al.; "Nucleophilic Reactivity; Part VIII. Kinetics of Reactions of Acetic Anhydride with Nucleophiles in Water," *Acta Chem. Scand.*, 27, 3572-3578 (1973).

N. De Kimpe, et al.; "Synthesis of 2,2-Dialkyl-1-aminocyclopropanecarboxylic Acids from α-Chloro Ketimines," *J. Org. Chem.* 55, 5777-5784 (1990).

M.J. Earle, et al.; "A New Synthesis of Primary Amines Using tert-Butylamine as an Ammonia Equivalent: The Triflic Acid Catalysed Removal of N-tert-Butyl Groups from Carbamates," *Synlett.*, 621-623 (1990).

J. Ritter, et al.; "A New Reaction of Nitriles. I. Amides from Alkenes and Mononitriles," *J. Am. Chem. Soc.*, 70, 4045-4048 (1948).

F. M. Callahan et al., "The Tertiary Butyl Group as a Blocking Agent for Hydrixyl Sulfhydryl and Amido Functions in Peptide Synthesis," *J. Am. Chem. Soc.*, 85, 201-7 (1963).

R.N. Lacey, "The Acid-catalysed Heterolysis of Amides with Alkyl-Nitrogen Fission ($A_{AL}$)," *J. Chem. Soc.* 1633-1639 (1960).

D. B. Reitz, et al., "A Directed Metalation of N-tert-Butyl-N-methyl-2-methoxybenzamide. Short Syntheses of 2-Methoxy-6-methylbenzoic Acid and Lunularic," *J. Org. Chem.*, 55, 1375-79 (1990).

F. Garro-Helion, et al., "Mild and Selective Palladium(0)-Catalyzed Deallylation of Allylic Amines. Allylamine and Diallylamine As Very Convenient Ammonia Equivalents for the Synthesis of Primary Amines," *J. Org. Chem.*, 58, 6109-13 (1993).

A. P. A. Arbore, et al., "A Rapid Approach to Amino-Acid Derivatives by [2,3]-Stevens Rearrangement," *Synlett*, 2, 236-38 (2000).

T.G. Greene, et al., *Protective Groups in Organic Synthesis*, 2nd Edition, John Wiley & Sons, Inc. New York, pp. 315-385 (1991).

A. Dobrev, et al., "Reaction D'Aminomercuration XI—Application A La Synthese De Morpholines," Tetrahedron Letters, 39, 4013-4016 (1972).

F. Fulop, et al., "Ring-Chain Tautomerism in Oxazolidines," *J. Org. Chem.* 58, 1967-1969 (1993).

F. Brion, "On the Lewis Acid Catalyzed Diels-Alder Reaction of Furan. Regio- and Stereospecific Synthesis of Substituted Cyclohexenols and Cyclohexadienols," *Tetrahedron Letters*, 23, 5299-5302 (1982).

C. M. Schueller et al., "Preparation of (R)-(+)-7-Oxabicyclo[2.2.1]hept-5-ene-exo-2-carboxylic Acid, a Precursor to Substrates for the Ring Opening Metathesis Polymerization," *Tetrahedron Letters*, 37, 8853-8856 (1996).

S. Vorwerk et al., "Carbocyclic Analogues of N-Acetyl-2,3-didehydro-2-deoxy-D-neuraminic Acid (Neu5Ac2en, DANA): Synthesis and Inhibition of Viral and Bacterial Neuraminidases," *Angew. Chem., Int. Ed.*, 37, 1732-1734 (1998).

J. March, "Reactions, Mechanisms, and Structure," Advanced Organic Chemistry, 4th Edition, John Wiley & Sons, New York, p. 352-357 (1992).

A. Dobrev, et al.,"Aminomercuration. Application to the Synthesis of Morpholines," Abstract #164618y, *Heterocycles*, 77, 411 (1972).

* cited by examiner

PROCESS FOR PREPARING 1,2-DIAMINO COMPOUNDS

BACKGROUND OF THE INVENTION

The present invention concerns a new multi-step process for preparing 1,2-diamino compounds from 1,2-epoxides, in particular 1,2-diamino compounds useful as inhibitors of viral or bacterial neuraminidases, a new step of that multi-step process for preparing 2-aminoalcohols from 1,2-epoxides, a new step for the transformation of a 2-aminoalcohol into a 1,2-diamino compound as well as specific intermediates useful in that multi-step process.

PCT Patent Publication No. 96/26933 describes a large class of compounds useful as inhibitors of viral or bacterial neuraminidases and their preparation. These compounds comprise a six-membered partially unsaturated carbocyclic or heterocyclic ring system, which can be substituted by several different substituents.

PCT Patent Publication No. 98/07685 discloses various methods for preparing compounds of the above class which are cyclohexene carboxylate derivatives. A particularly interesting compound is (3R,4R,5S)-5-amino-4-acetylamino-3-(1-ethyl-propoxy)-cyclohex-1-ene-carboxylic acid ethyl ester (C. U. Kim et al., J. Am. Chem. Soc., 1997, 119, 681–690). A method of preparation of that 1,2-diamino compound in 10 steps starting from shikimic acid, or in 12 steps starting from quinic acid, is described by J. C. Rohloff et al., J. Org. Chem., 1998, 63, 4545–4550. The 10 step method involves a final 4-step reaction sequence from the 1,2-epoxide (1S,5R,6R)-5-(1-ethyl-propoxy)-7-oxa-bicyclo[4.1.0]hept-3-ene-3-carboxylic acid ethyl ester via three potentially highly toxic and explosive azide intermediates. Dedicated know-how and expensive equipment are required to perform such a process. In a technical process, it is preferable to avoid use of azide reagents and azide intermediates.

U.S. Pat. No. 6,437,171 discloses an improved method for preparing 1,2-diamino compounds from 1,2-epoxides by using allylamine-magnesium bromide etherate to open the epoxide and allylamine-Brønsted acid to open the aziridine. Although this new method addresses the azide handling problem, it has a low overall yield from epoxide to final drug substance.

The problem to be solved by the present invention, therefore, is to find an azide-free process for preparing 1,2-diamino compounds from 1,2-epoxides that has higher overall yield.

That problem has been solved by the invention, as described below, and as defined in the appended claims.

SUMMARY OF THE INVENTION

The invention provides a process for preparing 1,2-diamino compounds of formula

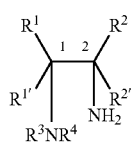

I and pharmaceutically acceptable addition salts thereof wherein, $R^1$, $R^{1'}$, $R^2$ and $R^{2'}$, independently of each other, are H, alkyl, alkenyl, alkynyl, cycloalkyl, cycloalkyl-lower alkyl, cycloalkyl-lower alkenyl, cycloalkyl-lower alkynyl, heterocyclyl, heterocyclyl-lower alkyl, heterocyclyl-lower alkenyl, heterocyclyl-lower alkynyl, aryl, aryl-lower alkyl, aryl-lower alkenyl, or aryl-lower alkynyl, or $R^1$ and $R^2$, $R^1$ and $R^{2'}$, $R^{1'}$ and $R^2$ or $R^{1'}$ and $R^{2'}$ taken together with the two carbon atoms to which they are bound, are a carbocyclic or heterocyclic ring system, or $R^1$ and $R^{1'}$ or $R^2$ and $R^{2'}$ taken together with the carbon atom to which they are bound, are a carbocyclic or heterocyclic ring system, with the proviso that at least one of $R^1$, $R^{1'}$, $R^2$ and $R^{2'}$ is not H, and $R^3$ and $R^4$, are independently a substituent of an amino group, and $R^3$ and $R^4$ are not both H which process is characterized in that it comprises the steps of:

a) reacting a 1,2-epoxide of formula

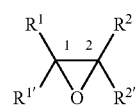

II wherein $R^1$, $R^{1'}$, $R^2$ and $R^{2'}$ are as above with an amine of formula $R^5NH_2$ wherein $R^5$ is a substituent of an amino group, but not H, to form a 2-aminoalcohol of formula

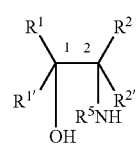

III wherein $R^1$, $R^{1'}$, $R^2$, $R^{2'}$ and $R^5$ are as above;

b) converting the 2-aminoalcohol of formula (III) to the aziridine of formula

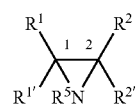

IV wherein $R^1$, $R^{1'}$, $R^2$, $R^{2'}$ and $R^5$ are as above;

c) reacting the aziridine of formula (IV) with an amine of formula $R^7NHR^8$, wherein $R^7$ and $R^8$, independently from each other, are H or a substituent of an amino group, with the proviso that not both $R^7$ and $R^8$ are H to obtain a 1,2-diamino compound of formula

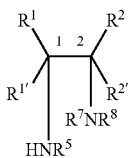

V wherein $R^1$, $R^{1'}$, $R^2$, $R^{2'}$, $R^5$, $R^7$ and $R^8$ are as above;

d) acylating the secondary amino group in position 1 of the 1,2-diamino compound of formula (V) to form an acylated 1,2-diamino compound of formula

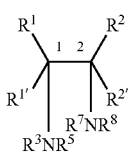

VI wherein $R^1$, $R^{1'}$, $R^2$, $R^{2'}$, $R^3$, $R^5$, $R^7$ and $R^8$ are as above;

e) removing $R^5$ from the acylated 1,2-diamino compound (VI) to produce an acylated 1,2-diamino compound of formula

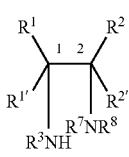

VII wherein $R^1$, $R^{1'}$, $R^2$, $R^{2'}$, $R^3$, $R^7$ and $R^8$ are as above; and, f) deprotecting the amino group in position 2 of the 1,2-diamino compound of formula (VII) to produce the 1,2-diamino compound of formula (I).

If desired, the resulting 1,2-diamino compound of formula (I) can be further transformed into a pharmaceutically acceptable addition salt.

DETAILED DESCRIPTION OF THE INVENTION

The term "alkyl" means a straight chain or branched saturated alkyl group with 1–20, preferably 1–12, C-atoms, which can carry one or more substituents.

The term "alkenyl" means a straight chain or branched alkenyl group with 2–20, preferably 2–12, C-atoms, which can carry one or more substituents.

The term "alkynyl" means a straight chain or branched alkynyl group with 2–20, preferably 2–12, C-atoms, which can carry one or more substituents.

The term "cycloalkyl" signifies a saturated, cyclic hydrocarbon group with 3–12, preferably 5–7, C-atoms, which can carry one or more substituents.

The term "aryl" denotes a mono-nuclear or di-nuclear aromatic group which can carry one or more substituents, for example, phenyl, substituted phenyl, naphthyl, or substituted naphthyl.

The term "heterocyclyl" means a saturated or unsaturated monocyclic or bicyclic group with 1 or 2 nitrogen, sulfur and/or oxygen atoms, for example, pyranyl, dihydropyranyl, tetrahydropyranyl, thiopyranyl, isobenzofuranyl, furanyl, tetrahydrofuranyl, thiofuranyl, dihydrothiofuranyl, benzo[b] dihydrofuranyl, tetrahydrothiofuranyl, thioxanyl, dioxanyl, dithianyl, chromanyl, isochromanyl, dithiolanyl, pyridyl, pyperidyl, imidazolidinyl, pyrrolidinyl, quinolyl or isoquinolyl, which can carry one or more substituents.

The term "carbocyclic ring system" means a cyclic alkyl group with 3–12, preferably 5–7, C-atoms, which can include one or two carbon-carbon double bonds, and which can carry one or more substituents, for example, cyclopentene, substituted cyclopentene, cyclohexene, substituted cyclohexene, cycloheptene, or substituted cycloheptene.

The term "heterocyclic ring system" means a monocyclic or bicyclic group with 1 or 2 nitrogen, sulfur and/or oxygen atoms, which can include one or two double bonds and carry one or more substituents, as exemplified above under the term "heterocyclyl", for example tetrahydropyran, dihydropyran, substituted dihydropyran, tetrahydrofuran, isobenzotetrahydrofuran, thioxan, 1,4-dioxane, dithian, dithiolan, piperidine, or piperazine.

Suitable substituents of the above groups are those which are inert in the reactions involved.

Examples of suitable substituents on such alkyl, alkenyl, alkynyl, cycloalkyl, cycloalkyl-lower alkyl, cycloalkyl-lower alkenyl, cycloalkyl-lower alkynyl, heterocyclyl, heterocyclyl-lower alkyl, heterocyclyl-lower alkenyl, heterocyclyl-lower alkynyl, aryl, or aryl-lower alkyl, aryl-lower alkenyl, aryl-lower alkynyl, are lower alkyl, lower alkoxy, lower alkyl carboxylate, carboxylic acid, carboxamide, N-(mono/di-lower alkyl)-carboxamide.

Examples of suitable substituents on such a carbocyclic or heterocyclic ring system are alkyl of 1 to 12 C-atoms, alkenyl of 2 to 12 C-atoms, alkynyl of 2 to 12 C-atoms, alkoxy of 1 to 12 C-atoms, alkyl of 1 to 12 C-atoms-carboxylate, carboxylic acid, carboxamide, N-(mono/di-alkyl of 1 to 12 C-atoms)-carboxamide. Preferred substituents are lower alkyl, lower alkenyl, lower alkynyl, lower alkoxy, carboxylic acid, lower alkyl carboxylate, carboxamide, N-(mono/di-lower alkyl)-carboxamide.

The term "lower" here denotes a group with 1–6, preferably 1–4, C-atoms. Examples of lower alkyl groups are methyl, ethyl, n-propyl, isopropyl, n-butyl, isobutyl, sec-butyl, tert-butyl, pentyl and its isomers and hexyl and its isomers. Examples of lower alkoxy groups are methoxy, ethoxy, propoxy, isopropoxy, n-butoxy, iso-butoxy, sec-butoxy, tert-butoxy and 1-ethyl-propoxy. Examples of lower alkyl carboxylates are methyl carboxylate, ethyl carboxylate, propyl carboxylate, isopropyl carboxylate and butyl carboxylate. Examples of lower alkanoyl groups are acetyl, propionyl and butyryl.

In accordance with the present invention, the term "substituent of an amino group" refers to any substituents conventionally used to hinder the reactivity of an amino group, as described in Green, T., "Protective Groups in Organic Synthesis", Chapter 7, John Wiley and Sons, Inc., 1991, 315–385, herein incorporated by reference. Such preferred substituents are acyl, alkyl, alkenyl, alkynyl, aryl-lower alkyl, silyl methyl wherein silyl is trisubstituted with lower alkyl, lower alkenyl, lower alkynyl and/or aryl. Advantageously, the reactivity of the amino group can also be hindered by protonation, e.g., with Lewis acids, including $H^+$.

The term "acyl" means alkanoyl, preferably lower alkanoyl, alkoxy-carbonyl, preferably lower alkoxy-carbonyl, aryloxy-carbonyl or aroyl such as benzoyl.

In a preferred embodiment the invention comprises a process for preparing 4,5-diamino-shikimic acid derivatives of formula

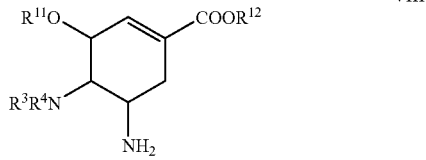

VIII and pharmaceutically acceptable addition salts thereof wherein
$R^{11}$ is an optionally substituted alkyl group, $R^{12}$ is an alkyl group and $R^3$ and $R^4$ independently of each other, are H or a substituent of an amino group, with the proviso that not both $R^3$ and $R^4$ are H from a cyclohexene oxide of formula

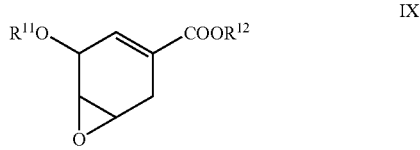

IX wherein $R^{11}$ and $R^{12}$ are as above.

The term alkyl in $R^{11}$ has the meaning of a straight chain or branched alkyl group of 1 to 20 C-atoms, preferably of 1 to 12 C-atoms. Examples of such alkyl groups are methyl, ethyl, n-propyl, i-propyl, n-butyl, i-butyl, tert-butyl, pentyl and its isomers, hexyl and its isomers, heptyl and its isomers, octyl and its isomers, nonyl and its isomers, decyl and its isomers, undecyl and its isomers and dodecyl and its isomers.

This alkyl group can be substituted with one or more substituents as defined in, e.g., WO 98/07685. Suitable substituents are alkyl having 1 to 20 C-atoms (as defined above), alkenyl having 2 to 20 C-atoms, cycloalkyl having 3 to 6 C-atoms, hydroxy, alkoxy having 1 to 20 C-atoms, alkoxycarbonyl having 1 to 20 C-atoms, F, Cl, Br, and I.

The preferred meaning for $R^{11}$ is 1-ethylpropyl.

$R^{12}$ here is a straight chain or branched alkyl group of 1 to 12 C-atoms, preferably of 1 to 6 C-atoms, as exemplified above.

The preferred meaning for $R^{12}$ is ethyl.

In the compound of formula (VIII), the substituent of an amino group is as defined above. Suitable substituents of amino groups are also described in, e.g., the WO 98/07685.

Preferred substituents of an amino group for $R^3$ and $R^4$ are alkanoyl groups, more preferably lower-alkanoyl with 1 to 6 C-atoms such as hexanoyl, pentanoyl, butanoyl (butyryl), propanoyl (propionyl), ethanoyl (acetyl) and methanoyl (formyl). Preferred alkanoyl group and therefore preferred meaning for $R^3$ is acetyl and for $R^4$ is H.

The preferred 1,2-diamino compound of formula (I) or 4,5-diamino-shikimic acid derivative of formula (VIII) therefore is the (3R,4R,5S)-5-amino-4-acetylamino-3-(1-ethyl-propoxy)-cyclohex-1-ene-carboxylic acid ethyl ester or the (3R,4R,5S)-5-amino-4-acetylamino-3-(1-ethyl-propoxy)-cyclohex-1-ene-carboxylic acid ethyl ester phosphate (1:1). The preferred 1,2-epoxide of formula (II) or cyclohexene oxide of formula (IX) therefore is the (1S,5R,6R)-5-(1-ethyl-propoxy)-7-oxa-bicyclo[4.1.0]hept-3-ene-3-carboxylic acid ethyl ester.

Step (a)

Step (a) comprises reacting a 1,2-epoxide of formula (II) with an amine of formula $R^5NH_2$ to form the respective 2-aminoalcohol of formula (III).

The amine of formula $R^5NH_2$ in step (a) is a primary amine which shows reactivity for opening the 1,2-epoxide ring.

$R^5$ in the amine of formula $R^5NH_2$ preferably is a straight chain or branched alkyl of 1 to 6 C-atoms.

The straight chain or branched alkyl of 1 to 6 C-atoms preferably is tert-butyl or an analog thereof such as tert-butyl or any branched alkyls with a tertiary carbon atom that is attached to the nitrogen. Suitable examples are, e.g., 2-methylbutyl and 2-methylpentyl. Preferred amines of formula $R_5NH_2$ with the meaning of a straight chain or branched alkyl of 1 to 6 C-atoms group therefore include tert-butylamine, 2-methylbutylamine, or 2-methylpentylamine, and more preferably tert-butylamine.

The preferred amine of formula $R^5NH_2$ is tert-butylamine.

The amine of formula $R^5NH_2$ is generally used in a molar amount of 1.0 to 3.0 equivalents, preferably of 1.5 to 2.5 equivalents, based on one equivalent of the 1,2-epoxide of formula (II).

Step (a) can be performed without a catalyst under normal or elevated pressure, however, the reaction time of step (a) can be significantly reduced in the presence of a catalyst.

Suitably the catalyst is a metal catalyst or a magnesium halide.

Convenient metal catalysts known to catalyze ring opening reactions of 1,2-epoxides with amines are lanthanide compounds such as lanthanide trifluoromethanesulfonates like Yb(OTf)$_3$, Gd(OTf)$_3$ and Nd(OTf)$_3$ (M. Chini et al., Tetrahedron Lett., 1994, 35, 433–436), samarium iodides (P. Van de Weghe, Tetrahedron Lett., 1995, 36, 1649–1652) or other metal catalysts such as amide cuprate reagents (Y. Yamamoto, J. Chem. Soc., Chem. Commun., 1993, 1201–1203) and Ti(O-i-Pr)$_4$ (M. Caron et al., J. Org. Chem., 1985, 50, 1557 and M. Müller, et al., J. Org. Chem., 1998, 68, 9753).

The ring opening with metal catalysts is carried out in the presence of an inert solvent such as tetrahydrofuran at temperatures between 20° C. and 150° C.

In accordance with the present invention, the magnesium halides are the preferred catalysts for the ring opening of 1,2-epoxides with amines. The term "magnesium halide derivative" here denotes anhydrous or hydrated magnesium chloride, magnesium bromide or magnesium iodide, or an etherate, in particular a dimethyl etherate, a diethyl etherate, a dipropyl etherate, or a diisopropyl etherate thereof.

Anhydrous magnesium chloride is the preferred catalyst.

The magnesium halide is suitably used in a molar amount of 50–120 mol %, preferably of 100 mol %.

Suitable solvents for the magnesium halide catalysis are protic solvents such as ethanol or methanol, or preferably an aprotic solvent such as tetrahydrofuran, dioxane, tert-butyl methyl ether, diisopropylether, isopropylacetate, ethylacetate, methylacetate, acetonitrile, benzene, toluene, pyridine, methylene chloride, dimethylformamide, N-methylformamide and dimethylsulfoxide or mixtures thereof.

The aprotic solvent is preferably selected from tetrahydrofuran, diisopropylether, tert-butyl methyl ether, acetonitrile, toluene or a mixture thereof, and more preferably is toluene or MTBE-acetonitrile.

Magnesium halide catalysis is advantageously carried out at temperatures between 0° C. and 200° C., preferably between 25° C. and 70° C.

The respective 2-aminoalcohol of formula (III) can be isolated after the reaction has been finished and if so desired purified by methods known to those skilled in the art.

Step (b)

Step (b) comprises converting the 2-aminoalcohol of formula (III) to the aziridine of formula (IV).

Because $R^5$ is a straight chain or branched alkyl of 1 to 6 C-atoms as outlined above in step (a), mesylation-cyclization is the major step for the conversion in step (b).

The mesylation is carried out by using a sufonylating agent such as halogenides or the anhydrides of the following sulfonic acids: methane sulfonic acid, p-toluenesulfonic acid, p-nitrobenzenesulfonic acid, p-bromobenzenesulfonic acid and trifluoromethanesulfonic acid.

Preferred sulfonylating agents are halogenides or anhydrides of methane sulfonic acid, such as, methanesulfonyl chloride.

The sulfonylating agent is preferably added in an amount of 1.0 to 2.0 equivalents relating to one equivalent of the 2-aminoalcohol of formula (III).

The mesylation-cyclization is advantageously carried out in an aqueous aprotic solvent, such as, methylene chloride or toluene.

The reaction temperature is preferably chosen in the range of 25° C. and 70° C.

Step (c)

Step (c) comprises converting the aziridine of formula (IV) to a 1,2-diamino compound of formula (V)

The amine of formula $R^7NHR^8$ of step (c) is a primary or secondary amine which shows reactivity for opening the aziridine ring.

$R^7$ or $R^8$ in the amine of formula $R^7NHR^8$ preferably is a straight chain or branched alkenyl of 2 to 6 C-atoms, optionally substituted benzyl or heterocyclyl methyl.

The straight chain or branched alkenyl of 2 to 6 C-atoms preferably is allyl or an analog thereof, such as, an allyl or allyl group which is substituted on the α-, β- or γ-carbon by one lower alkyl, lower alkenyl, lower alkynyl or aryl group. Suitable examples are, e.g., 2-methylallyl, 3,3-dimethylallyl, 2-phenylallyl, and 3-methylallyl. Preferred amines of formula $R^7NHR^8$ with the meaning of a straight chain or branched alkenyl of 1 to 6 C-atoms group therefore include allylamine, diallylamine or 2-methylallylamine, and more preferably, diallylamine.

Optionally substituted benzyl preferably is benzyl or benzyl analogs which are either substituted on the α-carbon atom with one or two lower alkyl, lower alkenyl, lower alkynyl or aryl groups or substituted on the benzene ring with one or more lower alkyl, lower alkenyl, lower alkynyl, lower-alkoxy or nitro groups. Suitable examples are α-methylbenzyl, α-phenylbenzyl, 2-methoxybenzyl, 3-methoxybenzyl, 4-methoxybenzyl, 4-nitrobenzyl or 3-methylbenzyl. Preferred amines of formula $R^7NHR^8$ with the meaning of an optionally substituted benzyl group include benzylamine, dibenzylamine, methylbenzylamine, 2-methoxybenzylamine, 3-methoxybenzylamine or 4-methoxybenzylamine, and more preferred is benzylamine.

Heterocyclyl methyl preferably is heterocyclyl methyl wherein either the methyl group is substituted with one or two lower alkyl, lower alkenyl, lower alkynyl or aryl groups or the heterocyclic ring is substituted with one or more lower alkyl, lower alkenyl, lower alkynyl or lower alkoxy groups. Suitable examples are furfuryl or picolyl.

The preferred amine of formula $R^7NHR^8$ is diallylamine.

The amine of formula $R^7NHR^8$ is generally used in a molar amount of 1.0 to 2.0 equivalents, preferably of 1.0 to 1.5 equivalents, based on one equivalent of the aziridine of formula (IV).

Step (c) can be performed without a catalyst under normal or elevated pressure, however, the reaction time of step (a) can, in general, be significantly reduced in the presence of a catalyst.

If either $R^7$ or $R^8$ is a benzyl group or a benzyl analog, the suitable catalysts can be ytterbium triflate (20 mol %) or lithium perchlorate (1 equivalent).

If $R^7NHR^8$ is an aliphatic amine, the suitable catalysts can be sulfonic acid and its derivatives, such as MsOH, $PhSO_3H$ and 10-Camphorsulfonic acid (CSA).

The sulfonic acid catalyst is preferably added in an amount of 1.0 to 2.0 equivalents relating to one equivalent of the aziridine of formula (IV).

Lewis acid catalysts (10–20 mol %) such as copper (II) chloride, bromide, or triflate, zinc chloride, zinc triflate, or boron trifluoride etherate are also suitable if excessive diallylamine is used.

The preferred catalysts are either 10-Camphorsulfonic acid and methanesulfonic acid.

The ring opening with sulfonic acid is carried out without solvent, neat, at temperatures between 100° C. and 120° C.

Step (d)

Step (d) comprises the acylation of the secondary amino group in position 1 of the 1,2-diamino compound of formula (V) to form an acylated 1,2-diamino compound of formula (VI).

Acylation can be effected under strong acidic conditions by treating the 1,2-diamino compound of formula (V) with acylating agents known to a person skilled in the art. The acylating agent can be an aliphatic or aromatic carboxylic acid, or an activated derivative thereof, such as an acyl halide, a carboxylic acid ester or a carboxylic acid anhydride. Suitable acylating agents are preferably acetylating agents such as acetylchloride, trifluoracteylchloride or acetic anhydride. A suitable aromatic acylating agent is benzoylchloride.

The reaction can be carried out without catalysts, but the yield is low in the absence of catalysts. The catalysts can be selected from pyridine and its derivatives such as N,N-dimethylaminopyridine (DMAP) or inorganic bases, such as sodium acetate, potassium acetate, tripotassium phosphate, potassium phosphate dibasic and calcium oxide.

Preferably, the acylation takes place under acidic conditions using a mixture of 0.5 to 2.0 equivalents of acetic anhydride using sodium acetate or pyridine as catalysts. The preferable catalyst is sodium acetate.

An inert solvent such as tert-butyl methyl ether may be added, it is however also possible to run the reaction without addition of any solvent.

The acetic anhydride is preferably added in an amount of 1.0 to 10.0 equivalents, preferably of 5 equivalents relating to one equivalent of the 1,2-diamino compound of formula (V). When the amount of acetic anhydride is between 1.5 to 5.0 equivalents, the rate of the reaction increases with the amount of acetic anhydride added.

The temperature is chosen in the range of 70° C. to 120° C., the preferred temperature is between 100° C. and 120° C.

Step (e)

Step (e) comprises removing the alkyl group from position 1 of the acylated 1,2-diamino compound (VI) to produce an acylated 1,2-diamino compound of formula (VII).

As the preferred meaning of $R^5$ is a tert-butyl group, the preferred process of Step (e) is removal of the tert-butyl group from the acylated 1,2-diamino of formula (VI).

The tert-butyl group of the acetamide of formula (VI) is cleaved by heating in acid, e.g., 2N HCl at reflux for prolonged period of time.

The preferred method for cleavage of the tert-butyl group from the acetamide of formula (VI) is with trifluoroacetic acid (TFA) at 25° C. or with hydrogen chloride in ethanol at reflux.

The TFA is preferably added in an amount of 1.0 to 10.0 equivalents, preferably of 5 equivalents, relating to one equivalent of the 1,2-diamino compound of formula (VI).

The temperature for the reaction using TFA is in the range of 25° C. to 50° C.

The hydrogen chloride in ethanol is preferably added in an amount of 1.0 to 2.0 equivalents relating to one equivalent of the 1,2-diamino compound of formula (VI).

The temperature for the reaction using hydrogen chloride in ethanol is in the range of 50° C. to 70° C., preferably at 64° C.

An inert solvent may be added, it is however also possible to run the reaction without addition of any solvent.

Step (f)

Step (f) comprises deprotecting the amino group in position 2 of the 1,2-diamino of formula (VII) and, if desired, further transforming the resulting 1,2-diamino compound of formula (I) into a pharmaceutically acceptable addition salt.

Deprotecting the amino group, i.e., removal of the substituent of the amino group in position 2 is dependent on the residue $R^7$ and $R^8$.

Because the preferred meanings for $R^7$ and $R^8$ are straight chain or branched alkenyl of 2 to 6 C-atoms as outlined above in step (c), removal of the alkenyl group takes place in the presence of a suitable metal catalyst, preferably a precious metal catalyst such as Pt, Pd or Rh, either applied on an inert support, such as charcoal or alumina, or in complexed form. Because the preferred amine of $R^7NHR^8$ is diallylamine according to step (c), a preferred catalyst is palladium acetate, and a more preferred catalyst is tetrakis (triphenylphosphine) palladium in the presence of 1,3-dimethylbarbituric acid (NDMBA) which serves as an allyl-transfer acceptor.

For example, the reaction is effectively carried out with 1 mol % of palladium acetate relating to the 1,2-diamino of formula (VII). Lower charges of the catalyst (0.1–0.5 mol %) also work, but reaction time is longer.

The NDMBA is preferably added in an amount of 0.6 to 1.5 equivalents relating to one equivalent of the 1,2-diamino of formula (VII).

The removal of the alkenyl group is advantageously carried out in an aqueous solvent. The solvent itself can be protic or aprotic. Suitable protic solvents are, e.g., alcohols such as methanol, ethanol and isopropanol. Suitable aprotic solvents are, e.g., acetonitrile, tetrahydrofurane (THF), toluene, and dioxane. The preferred solvent is ethanol.

The reaction temperature is preferably in the range of 20° C. and 70° C.

The 1,2-diamino compound of formula (I) can be isolated, e.g., by evaporation and crystallization, but it is preferably kept in, e.g., an ethanolic solution and then further transformed into a pharmaceutically acceptable addition salt following the methods described in J. C. Rohloff et al., J. Org. Chem., 1998, 63, 4545–4550; WO 98/07685).

The term "pharmaceutically acceptable acid addition salts" embraces salts with inorganic and organic acids, such as hydrochloric acid, hydrobromic acid, nitric acid, sulfuric acid, phosphoric acid, citric acid, formic acid, fumaric acid, maleic acid, acetic acid, succinic acid, tartaric acid, methane sulfonic acid, p-toluenesulfonic acid, and the like.

The salt formation is effected in accordance with methods which are known per se and which are familiar to one skilled in the art. Not only salts with inorganic acids, but also salts with organic acids come into consideration. Hydrochlorides, hydrobromides, sulfates, nitrates, citrates, acetates, maleates, succinates, methansulfonates, p-toluenesulfonates and the like are examples of such salts.

Preferred pharmaceutically acceptable acid addition salt is the 1:1 salt with phosphoric acid which can be formed, preferably, in ethanolic solution at a temperature of −20° C. to 50° C.

The invention also relates to the following new intermediates:

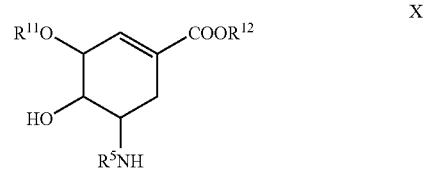

X wherein $R^5$, $R^{11}$ and $R^{12}$ are as stated above, or an addition salt thereof.

A preferred representative of the compounds of formula (X) is ethyl (3R,4S,5R)-5-N-(1,1-Dimethylethyl)amino-3-(1-ethylpropoxy)-4-hydroxy-cyclohexene-1-carboxylate (with $R^{11}$=1-ethyl-propyl, $R^{12}$=ethyl, and $R^5$=tert-butyl).

An additional new intermediate is a compound of formula (XI):

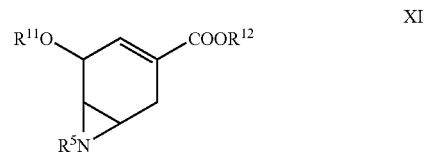

XI wherein $R^5$, $R^{11}$ and $R^{12}$ are as stated above, or an addition salt thereof.

A preferred representative of compounds of formula (XI) is ethyl (3R,4S,5R)-4,5-(1,1-Dimethylethyl)imino-3-(1-ethylpropoxy)-1-cyclohexene-1-carboxylate (with $R^{11}$=1-ethyl-propyl, $R^{12}$=ethyl, and $R^5$=tert-butyl).

Another new intermediate from the invention is a compound of formula (XII):

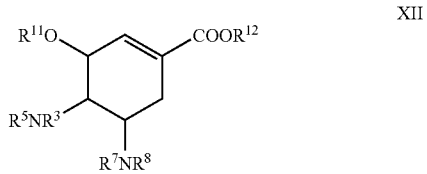

XII wherein $R^3$, $R^5$, $R^7$, $R^8$, $R^{11}$ and $R^{12}$ are as stated above or an addition salt. thereof.

Preferred representatives of compounds of formula (XII) are ethyl (3R,4R,5S)-5-N,N-Diallylamino-4-(1,1-dimethylethyl)amino-3-(1-ethylpropoxy)-1-cyclohexene-1-carboxylate (with $R^{11}$=1-ethyl propyl, $R^{12}$=ethyl, $R^5$=tert-butyl, $R^3$=H, $R^7$=allyl, $R^8$=allyl), ethyl (3R,4R,5S)-4-N-Acetyl(1,1-dimethylethyl)amino-5-N,N-diallylamino-3-(1-ethylpropoxy)-1-cyclohexene-1-carboxylate (with $R^{11}$=1-ethyl propyl, $R^{12}$=ethyl, $R^5$=tert-butyl, $R^3$=acetyl, $R^7$=allyl, $R^8$=allyl) and ethyl (3R,4R,5S)-4-N-Acetyl(1,1-dimethylethyl)amino-5-N,N-diallylamino-3-(1-ethylpropoxy)-1-cyclohexene-1-carboxylate hydrochloride (with $R^{11}$=1-ethyl propyl, $R^{12}$=ethyl, $R^5$=tert-butyl, $R^3$=acetyl, $R^7$=allyl, $R^8$=allyl).

The invention also relates to a new process for preparing a 2-aminoalcohol of formula

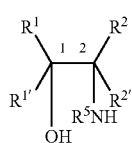

III wherein $R^1$, $R^{1'}$, $R^2$ and $R^{2'}$, independently from each other, are H, alkyl, alkenyl, alkynyl, cycloalkyl, cycloalkyl-lower alkyl, cycloalkyl-lower alkenyl, cycloalkyl-lower alkynyl, heterocyclyl, heterocyclyl-lower alkyl, heterocyclyl-lower alkenyl, heterocyclyl-lower alkynyl, aryl, or aryl-lower alkyl, aryl-lower alkenyl, aryl-lower alkynyl, or $R^1$ and $R^2$, $R^1$ and $R^{2'}$, $R^{1'}$ and $R^2$ or $R^{1'}$ and $R^{2'}$ taken together with the two carbon atoms to which they are bound, are a carbocyclic or heterocyclic ring system, or $R^1$ and $R^{1'}$ or $R^2$ and $R^{2'}$ taken together with the carbon atom to which they are bound, are a carbocyclic or heterocyclic ring system, with the proviso that at least one of $R^1$, $R^{1'}$, $R^2$ and $R^{2'}$ is not H, and $R^5$ is a substituent of an amino group but not H, comprising treating a 1,2-epoxide of formula

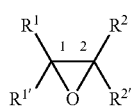

II wherein $R^1$, $R^{1'}$, $R^2$ and $R^{2'}$ are as above with an amine of formula $R^5NH_2$ wherein $R^5$ is as described above, in the presence of a magnesium halide catalyst.

This process corresponds to the preferred method of step a) as described herein. Accordingly, the respective description of step a) is incorporated herein by reference.

Preferred amines of formula $R^5NH_2$ accordingly are tert-butylamine, 2-methylbutylamine, and 2-methylpentylamine, and more preferably, tert-butylamine, and the preferred magnesium halide catalyst is magnesium chloride.

The invention further relates to a new process for the transformation of the acylated 1,2-diamino compound of formula (VI)

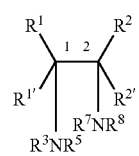

VI wherein $R^1$, $R^{1'}$, $R^2$, $R^{2'}$, $R^3$, $R^5$, $R^7$ and $R^8$ are as above, into an acylated 1,2-diamino compound of formula (VII)

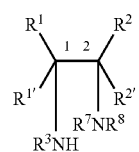

VII wherein $R^1$, $R^{1'}$, $R^2$, $R^{2'}$, $R^3$, $R^7$ and $R^8$ are as above.

This process corresponds to step e) as described herein before. Accordingly, the whole description of step e) is incorporated herein by reference. Also, the same preferences as given under step e) apply here.

As stated above, this process comprises removing the alkyl group from the nitrogen at position 1 of the acylated 1,2-diamino of formula VI.

The invention is further illustrated by the following examples.

EXAMPLE 1

Preparation of (3R,4R,5S)-5-amino-4-acetylamino-3-(1-ethyl-propoxy)-cyclohex-1-ene-carboxylic acid ethyl ester from (1S,5R,6R)-5-(1-ethyl-propoxy)-7-oxa-bicyclo[4.1.0]hept-3-ene-3-carboxylic acid ethyl ester.

a) Preparation of ethyl (3R,4S,5R)-5-N-(1,1-Dimethylethyl)amino-3-(1-ethylpropoxy)-4-hydroxy-cyclohexene-1-carboxylate In a 500 ml 3-necked round bottom flask equipped with a condenser with dry nitrogen adapter, an overhead paddle stirrer and a septum with teflon thermocouple, 21.1 mL (14.67 g, 200.6 mmol, 1.7 equivalents) of tert-butylamine are added to a suspension of 21.32 g (82.6 mmol, 70 mol %) of magnesium bromide etherate in 70 mL dry toluene at 25° C. (cool H$_2$O bath), the resulting colorless slurry is stirred for 60 min. In a 100 mL 1-necked round bottomed flask capped with a septum, a solution of 30.00 g (118.00 mmol) of (1S,5R,6S)-5-(1-ethyl-propoxy)-7-oxa-bicyclo[4.1.0]hept-3-ene-3-carboxylic acid ethyl ester in 60 mL dry toluene is prepared, which is then added via 18 gauge stainless steel cannula to the magnesium bromide-amine complex suspension at 20–25° C. The resulting suspension is heated at 50° C. (silicon oil bath) for 23 h.

After cooling the suspension to 25° C., 57 mL of 2.5 M ammonium chloride solution are added and the resulting suspension is stirred at 25° C. for 30 min. Solids are removed by suction filtration and the layers separated. The organic layer is concentrated in vacuo (rotary evaporator at 35° C. and 25 mm Hg then vacuum pump at 25° C. and 1 mm Hg for 17 h) to yield as crude product 37.73 g (Theoretical 38.63 g) of ethyl (3R,4S,5R)-5-N-(1,1-Dimethylethyl)amino-3-(1-ethylpropoxy)-4-hydroxy-cyclohexene-1-carboxylate as an orange oil with trace solids. An analytical sample is prepared by radial chromatography on silica gel.

$^1$H NMR (CDCl$_3$) δ 6.84–6.82 (m, 1H), 4.23 (t, 1H, J=4.0 Hz), 4.20 (q, 2H, J=7.0 Hz), 3.6–3.0 (broad, 1H, NH or OH), 3.55 (p, 1H, J=6.0 Hz), 3.37 (dd, 1H, J=4.0 Hz, J=9.5 Hz), 3.12–3.08 (m, 1H, J=5.0 Hz), 2.91 (dd, 1H, J=5.5 Hz, J=17 Hz), 1.97–1.91 (m, 1H, J=8.0 Hz, J=17 Hz), 1.59–1.54 (m, 4H), 1.29 (t, 3H, J=7.0 Hz), 1.13 (s, 9H), 0.95 (t, 3H, J=7.5 Hz), 0.91 (t, 3H, J=7.5 Hz).

$^{13}$C NMR (CDCl$_3$) δ166.9, 135.7, 131.7, 82.8, 72.6, 71.3, 61.0, 51.3, 48.9, 34.3, 30.5, 26.8, 26.7, 14.5, 10.4, 9.5.

IR (neat) 3600–3300, 2970, 2940, 2880, 1720, 1660, 1470, 1400, 1370, 1240, 1110, 1080, 1060, 670 cm$^{-1}$.

HRFABMS found m/z 328.2481 (M+H$^+$), calcd for C$_{18}$H$_{34}$NO$_4$, 328.2488.

(b) Preparation of Ethyl (3R,4S,5R)-4,5-(1,1-Dimethylethyl)imino-3-(1-ethylpropoxy)-1-cyclohexene-1-carboxylate In a 500 ml 3-necked round bottom flask equipped with a condenser with dry nitrogen adapter, an overhead paddle stirrer and a septum with teflon thermocouple, 9.36 mL of methanesulfonyl chloride (13.86 g, 121.0 mmol, 1.05 equivalents) are added to a solution of 37.73 g crude tert-butylamino alcohol obtained according to (a) in 150 mL dry toluene at 20–25° C. (cool H$_2$O bath) over 6min. The resulting solution is stirred at 25° C. for 60 min. 32.1 mL of triethylamine (23.31 g, 230.4 mmol, 2.0 equivalents) are then added, dropwise, at 20–30° C. (cool H$_2$O bath) over 12 min. The resulting suspension is stirred at 25° C. for 67 min and then heated at 70° C. (silicon oil bath) for 3 h.

After the suspension is cooled down to 25° C., a solution of 16.7 g (120.8 mmol) of anhydrous potassium carbonate in 60 mL H$_2$O are added. The suspension is stirred for 15 min before the layers are separated. The organic layer is concentrated in vacuo (rotary evaporator at 35° C. and 25 mm Hg then vacuum pump at 25° C. and 1 mm Hg for 17 h) to yield 35.66 g (Theoretical 35.65 g) of crude ethyl (3R,4S,5R)-4,5-(1,1-Dimethylethyl)imino-3-(1-ethylpropoxy)-1-cyclohexene-1-carboxylate in the form of an orange oil with trace solids. An analytical sample is prepared by radial chromatography on silica gel.

$^1$H NMR (CDCl$_3$) δ 6.80–6.78 (m, 1H), 4.17 (dq, 2H, J=7.5 Hz, J=1.5 Hz), 4.15–4.14 (m 1H), 3.39 (p, 1H, J=6.0 Hz), 2.62–2.52 (m, 2H), 2.13–2.11 (m, 1H), 2.00 (d, 1H, J=6.0 Hz), 1.61–1.51 (m, 4H), 1.26 (t, 3H, J=7.5 Hz), 1.00 (s, 9H), 0.98 (t, 3H, J=7.5 Hz), 0.92 (t, 3H, J=7.5 Hz).

$^{13}$C NMR (CDCl$_3$) δ 167.3, 134.4, 128.6, 82.4, 70.9, 60.7, 53.3, 33.2, 29.9, 27.0, 26.9, 26.8, 25.0, 14.5, 10.2, 9.9.

IR (neat) 3575, 2970, 2930, 2875, 1720, 1650, 1460, 1370, 1250, 1230, 1215, 1080, 1070, 1050, 670 cm$^{-1}$.

HRFABMS found m/z 310.2378 (M+H$^+$), calcd for C$_{18}$H$_{32}$NO$_3$, 310.2382.

(c) Preparation of ethyl (3R,4R,5S)-5-N,N-Diallylamino-4-(1,1-dimethylethyl)amino-3-(1-ethylpropoxy)-1-cyclohexene-1-carboxylate In a 500 mL 1-necked, round-bottomed flask equipped with a condenser, a dry nitrogen adapter and a magnetic stir bar, 29.45 g of 10-Camphorsulfonic acid (126.8 mmol, 1.1 equivalents) are added to a mixture of 35.66 g of the ethyl (3R,4S,5R)-4,5-(1,1-Dimethylethyl)imino-3-(1-ethylpropoxy)-1-cyclohexene-1-carboxylate as obtained from (b) and 17.1 mL (13.44 g, 138.3 mmol, 1.2 equivalents) of diallylamine. The resulting suspension is heated at 120° C. (silicon oil bath) for 4 h.

The suspension is cooled to 25° C. and a solution of 5.27 g (132 mmol) of sodium hydroxide in 70 mL H$_2$O is added. The suspension is stirred for 15 min before the layers are separated. The organic layer is concentrated in vacuo (rotary evaporator at 35° C. and 25 mm Hg then vacuum pump at 25° C. and 1 mm Hg for 18 h) to yield 44.00 g (Theoretical 46.86 g) of ethyl (3R,4R,5S)-5-N,N-Diallylamino-4-(1,1-dimethylethyl) amino-3-(1-ethylpropoxy)-1-cyclohexene-1-carboxylate as a brown oil with trace solids. An analytical sample is prepared by radial chromatography on silica gel.

$^1$H NMR (CDCl3) δ 6.87 (t, 1H, J=2.5 Hz), 5.79 (m, 2H), 5.17 (d, 2H, J=17.5 Hz), 5.11 (d, 2H, J=10.5 Hz), 4.22 (q, 2H, J=7.0 Hz), 3.94–3.92 (m, 1H), 3.41–3.36 (m, 1H), 3.31–3.27 (dm, 2H, J=14 Hz), 2.92 (dd, 2H, J=14 Hz, J=8.0 Hz), 2.81 (dd, 1H, J=10.5 Hz, J=6.5 Hz), 2.69 (dt, 1H, J=10.5 Hz, J=4.5 Hz), 2.56 (dd, 1H, J=17.0 Hz, J=4.5 Hz), 2.19 (dt, 1H, J=17.0 Hz, J=3 Hz), 1.82–1.74 (m, 1H), 1.64–1.56 (m, 1H), 1.51–1.38 (m, 2H), 1.31 (t, 3H, J=7.0 Hz), 1.15 (s, 9H), 0.91 (t, 3H, J=7.5 Hz), 0.87 (t, 3H, J=7.5 Hz).

$^{13}$C NMR (CDCl$_3$) δ 167.1, 137.9, 136.9, 130.3, 117.7, 80.1, 78.8, 60.9, 58.5, 55.3, 52.6, 50.7, 31.1, 26.7, 25.3, 22.5, 14.5, 10.5, 9.87.

IR (neat) 3590, 3640–3000, 2980, 2930, 2875, 2820, 1720, 1665, 1640, 1230, 675 cm$^{-1}$.

HRFABMS found m/z 407.3280 (M+H$^+$), calcd for C$_{24}$H$_{43}$N$_2$O$_3$, 407.3274.

(d) Preparation of ethyl (3R,4R,5S)-4-N-Acetyl(1,1-dimethylethyl)amino-5-N,N-diallylamino-3-(1-ethylpropoxy)-1-cyclohexene-1-carboxylate In a 500 mL 1-necked, round-bottomed flask equipped with a condenser, a dry nitrogen adapter and a magnetic stir bar, 20.4 mL of acetic anhydride (22.09 g, 216.4 mmol, 2.0 equivalents) are added to a mixture of 44.00 g of the ethyl (3R,4R,5S)-5-N,N-Diallylamino-4-(1,1-dimethylethyl) amino-3-(1-ethylpropoxy)-1-cyclohexene-1-carboxylate as prepared in (c) and 44 mL dry pyridine at 20–25° C. (cool H$_2$O bath). The resulting clear brown solution is heated at 100° C. (silicon oil bath) for 22 h.

The solution is cooled to 25° C. and 40 mL of pyridine are recovered in vacuo (rotary evaporator at 35° C. and 15 mm Hg). The residual oil is taken up in 150 mL of toluene. A solution of 14.00 g (350 mmol) of sodium hydroxide in 45 mL H$_2$O is prepared and 50 mL of this NaOH solution are added to the mixture. The suspension is then stirred for 15 min before the layers are separated. The organic layer is concentrated in vacuo (rotary evaporator at 35° C. and 25 mm Hg then vacuum pump at 25° C. and 1 mm Hg for 19 h) to yield 49.52 g of opaque brown oil with solids.

The brown oil (49.52 g) is taken up in 250 mL hexanes and 12.5 g of activated carbon, for example Darco G60™, was added. After stirring for 15 min, the suspension is suction filtered through a pad of 10.0 g silica-alumina 135. The filter cake is rinsed with 50 mL fresh hexanes. The combined mother liquors are concentrated in vacuo (rotary evaporator at 30° C. and 80 mm Hg then vacuum pump at 25° C. and 1 mm Hg for 25 h) to yield 42.56 g (Theoretical 48.12 g) of ethyl (3R,4R,5S)-4-N-Acetyl(1,1-dimethylethyl) amino-5-N,N-diallylamino-3-(1-ethylpropoxy)-1-cyclohexene-1-carboxylate as an orange syrup. An analytical sample is prepared by radial chromatography on silica gel. The hydrochloride salt is prepared then recrystallized from ethyl acetate to afford colorless needles, m.p. 131–133° C. (dec with gas evolution).

For the free base:

$^1$H NMR (CDCl$_3$) δ 6.87 (m, 1H), 5.81–5.73 (m, 2H), 5.12 (d, 2H, J=17 Hz), 5.07 (d, 2H, J=10.5 Hz), 5.02–4.85 (br), 4.22 (dt, 2H, J=7 Hz), 3.85–3.75 (br), 3.58–3.46 (br), 3.28 (br), 3.24 (br d, 2H, J=14 Hz), 2.88 (dd, 2H, J=14 Hz, J=8 Hz), 2.46–2.38 (m, 2H), 2.28–2.18 (br, 3H), 1.88 (br), 1.63–1.54 and 1.44–1.34 (m, m, 4H), 1.51 (s, 9H), 1.31 (t, 3H, J=7 Hz), 0.93 (t, 3H, J=7.5 Hz), 0.81 (t, 3H, J=7.5 Hz).

$^{13}$C NMR (CDCl$_3$) δ 172.5, 166.8, 140.5, 137.2, 130.7, 117.1, 79.5, 73.2, 62.2, 60.9, 56.0, 53.2, 32.2, 31.8, 27.2, 26.6, 25.4, 23.6, 14.5, 10.0, 9.9.

IR (neat) 3570, 3090, 2975, 2940, 2880, 2820, 1720, 1625, 1475, 1450, 1370, 1240, 1120, 1060, 675 cm$^{-1}$.

HRFABMS found m/z 449.3368 (M+H$^+$), calcd for C$_{26}$H$_{45}$N$_2$O$_4$, 449.3379.

For the hydrochloride salt:

$^1$H NMR (CDCl$_3$) δ 6.97 (br, 1H), 6.61–6.51 (m, 1H), 6.35–6.25 (m, 1H), 5.53–5.39 (m, 4H), 5.01–4.98 (br d, 1H), 4.77–4.70 (m, 1H), 4.26 (q, 2H, J=7 Hz), 4.24–4.18 (br, 1H), 4.06–3.99 (br, 1H), 3.88 (br t, 1H), 3.51–3.44 (m, 1H), 3.41–3.33 (m, 1H), 3.33–3.27 (m, 1H), 2.80–2.73 (br d, 1H), 2.66–2.58 (m, 1H), 2.62 (m, 1H), 2.54 (s, 3H), 1.68 (s, 9H), 1.68–1.54 (m, 2H), 1.46–1.34 (m, 2H), 1.34 (t, 3H, J=7 Hz), 0.96 (t, 3H, J=7.5 Hz), 0.82 (t, 3H, J=7.5 Hz).

$^{13}$C NMR (CDCl$_3$) δ 175.9, 165.5, 140.0, 128.3, 127.4, 127.0, 125.1, 124.0, 79.7, 71.0, 61.4, 59.3, 58.9, 58.2, 55.4, 53.0, 32.5, 28.1, 26.6, 25.1, 24.2, 14.3, 10.1, 10.0.

(e) Preparation of ethyl (3R,4R,5S)-4-N-Acetylamino-5-N,N-diallylamino-3-(1-ethylpropoxy)-1-cyclohexene-1-carboxylate In a 500 mL 1-necked, round-bottomed flask equipped with a dry nitrogen adapter and a magnetic stir bar, 210 mL of precooled (0–5° C.) trifluoroacetic acid (311 g) is added to 42.56 g of the ethyl (3R,4R,5S)-4-N-Acetyl(1,1-dimethylethyl)amino-5-N,N-diallylamino-3-(1-ethylpropoxy)-1-cyclohexene-1-carboxylate as obtained from (d), and the solution is stirred at 25° C. for 5.5 h. Trifluoroacetic acid (~145 mL) is then distilled in vacuo (rotary evaporator at 30° C. and 90 to 30 mm Hg). 150 mL of toluene-hexanes (1:1, v:v) is added and the solution was again concentrated in vacuo (rotary evaporator at 30° C. and 80 to 30 mm Hg). The residual oil (80 g) is diluted with 150 mL of 1:1 (v:v) toluene-hexanes before 150 mL of saturated sodium carbonate solution are added. The suspension is stirred for 15 min, then 150 mL water are added, and the layers separated. The aqueous layer is extracted with 50 mL of 1:1 (v:v) toluene-hexanes. The combined organic layers are extracted twice with 3.0 M HCl (first time 30 mL and second time 15 mL). The combined aqueous layers are diluted with 100 mL toluene and a solution, prepared by dissolving 5.67 g (142 mmol) of sodium hydroxide in 17 mL of H$_2$O, is added at 20–25° C. (ice-water bath) (aqueous=pH 13–14). The layers are separated and the aqueous layer is extracted with 50 mL toluene three times. The combined toluene extracts are dried (MgSO$_4$), filtered, and concentrated in vacuo (rotary evaporator at 35° C. and 25 mm Hg) to yield 38.73 g of brown syrup.

The syrup is triturated five times with hexanes (first time 200 mL then 100 mL for four times) at 25° C. The supernatant is decanted after each time. The final suspension is suction filtered and the solid dried in vacuo (vacuum pump at 25° C. and 1 mm Hg for 17 h) to yield 26.76 g (Theoretical 37.24 g, 5-step yield 72%) of ethyl (3R,4R,5S)-4-N-Acetylamino-5-N,N-diallylamino-3-(1-ethylpropoxy)-1-cyclohexene-1-carboxylate with some slightly tacky beige solid. An analytical sample was prepared by recrystallization from heptane-ethyl acetate, m.p. 101.8–102.3° C.

$^1$H NMR (CDCl$_3$) δ 6.73 (m, 1H), 5.76–5.68 (m, 2H), 5.35 (d, 1H), 5.16 (d, 2H, J=16.5 Hz), 5.07 (d, 2H, J=10 Hz), 4.21 (q, 2H, J=7 Hz), 4.08 (dm, 1H, J=9 Hz), 3.91 (dt, 1H, J=11.5 Hz, J=9 Hz), 3.32 (p, 1H, J=5.5 Hz), 3.28 (dm, 2H, J=14.5 Hz), 3.05 (dt, 1H, J=11.5 Hz, J=5 Hz), 2.92 (dd, 2H, J=14.5 Hz, J=7.5 Hz), 2.58 (dd, 1H, J=17 Hz, J=5 Hz), 2.17 (ddt, 1H, J=17 Hz, J=10.5 Hz, J=3.5 Hz) 2.00 (s, 3H), 1.54–1.47 (m, 4H), 1.30 (t, 3H, J=7 Hz), 0.91 (t, 3H, J=7 Hz), 0.87 (t, 3H, J=7 Hz).

$^{13}$C NMR (CDCl$_3$) δ 170.4, 166.9, 138.5, 137.3, 129.9, 116.9, 82.4, 77.7, 61.1, 56.5, 53.5, 52.5, 26.3, 25.8, 23.9, 23.7, 14.5, 9.8, 9.5.

IR (KBr) 3270, 3110, 2980–2960, 2930, 2880, 2810, 1720, 1650, 1580, 1470, 1450, 1380, 1270, 1235, 1120, 1075, 1055, 925 cm$^{-1}$.

HRFABMS found m/z 393.2756 (M+H$^+$), calcd for C$_{22}$H$_{37}$N$_2$O$_4$, 393.2753.

Anal. Calcd for C$_{22}$H$_{36}$N$_2$O$_4$: C, 67.32; H, 9.24; N, 7.14. Found: C, 67.00; H, 9.42; N, 7.03.

(f) Preparation of ethyl (3R,4R,5S)-4-N-Acetylamino-5-amino-3-(1-ethylpropoxy)-1-cyclohexene-1-carboxylate A 50 mL airlessware flask (N$_2$-vacuum line on sidearm) equipped with a septum and a magnetic stir bar is charged with 1.874 g of 1,3-Dimethylbarbituric Acid (NDMBA) (12.00 mmol). The flask is sealed and the atmosphere is changed to dry nitrogen (10 nitrogen-vacuum cycles). The flask is transferred to a glove bag and 50.0 mg (0.0433 mmol) of tetrakis (triphenylphosphine) palladium is charged.

A solution of 3.925 g (10.00 mmol) of the ethyl (3R,4R,5S)-4-N-Acetylamino-5-N,N-diallylamino-3-(1-ethylpropoxy)-1-cyclohexene-1-carboxylate prepared as in (e) in 5 mL of dry THF is prepared in a 15 mL 1-necked flask capped with a septum (10 nitrogen-vacuum cycles prior to adding THF). This solution is then transferred to the reaction flask using a 20-gauge stainless steel cannula. The transfer is completed using 2 mL of fresh dry THF. The resulting yellow suspension is heated at 50° C. for 133 min.

The suspension is cooled to 25° C. and 10 mL toluene and 8 mL 1.5 M HCl are added. The layers are separated (aqueous pH=1). The aqueous layer is washed with 10 mL of toluene three times. A solution of 0.52 g (13 mmol) NaOH in 1.5 mL H$_2$0 is slowly added to the aqueous layer (aqueous pH=12). 5 mL of brine are then added. The resulting suspension is extracted with 10 mL of isopropyl acetate three times. The combined extracts are concentrated in vacuo (rotary evaporator at 30–35° C. and 60 mm Hg, hexanes trituration, then vacuum pump at 25° C. and 1 mm Hg for 16 h) to yield 2.770 g (Theoretical 3.124 g, 88.7% yield) of ethyl (3R,4R,5S)-4-N-Acetylamino-5-amino-3-(1-ethylpropoxy)-1-cyclohexene-1-carboxylate as a colorless solid.

EXAMPLE 2

Preparation of (3R,4R,5S)-5-amino-4-acetylamino-3-(1-ethyl-propoxy)-cyclohex-1-ene-carboxylic acid ethyl ester from (1S,5R,6R)-5-(1-ethyl-propoxy)-7-oxa-bicyclo[4.1.0]hept-3-ene-3-carboxylic acid ethyl ester.

Steps (a), (b) and (c) are performed as described supra, in Example 1.

(d1) Preparation of ethyl (3R,4R,5S)-4-N-Acetyl(1,1-dimethylethyl)amino-5-N,N-diallylamino-3-(1-ethylpropoxy)-1-cyclohexene-1-carboxylate In a 500 mL 1-necked, round-bottomed flask equipped with a Claisen adapter, an overhead (paddle) stirrer, and a water-cooled condenser with dry nitrogen adapter, 40.9 mL of acetic anhydride (44.2 g, 433 mmol, 4.83 equivalents) are added to a mixture of 45.55 g (36.49 g or 89.7 mmol at 80.1 wt %) of the ethyl (3R,4R,5S)-5-N,N-Diallylamino-4-(1,1-dimethylethyl)amino-3-(1-ethylpropoxy)-1-cyclohexene-1-carboxylate as obtained from (c) and 10.66 g (130 mmol, 1.45 equivalents) of anhydrous sodium acetate. The resulting suspension is heated at 120° C. (silicon oil bath) for 4 h.

The suspension was cooled to 25° C., diluted with 150 mL heptane, cooled to −5° C., then quenched by dropwise addition of a solution prepared by dissolving 31.0 g (776 mmol) of sodium hydroxide in 155 mL $H_2O$ (153.4 g) over 40 min at −5 to 0° C. The resulting suspension is warmed to 25° C. then stirred for 30 min. The layers are separated, and the aqueous layer extracted with 25 mL of heptane. The combined organic layers are washed with 25 mL of $H_2O$ and then concentrated in vacuo (rotary evaporator at 30° C. and 40–10 mm Hg) to yield 49.72 g of ethyl (3R,4R,5S)-4-N-Acetyl(1,1-dimethylethyl)amino-5-N,N-diallylamino-3-(1-ethylpropoxy)-1-cyclohexene-1-carboxylate (LC assay 81.6 wt %, Theoretical 40.26 g, 100.8% yield) as a brown syrup with trace solids.

(d2) Preparation of Ethyl (3R,4R,5S)-4-N-Acetyl(1,1-dimethylethyl)amino-5-N,N-diallylamino-3-(1-ethylpropoxy)-1-cyclohexene-1-carboxylate hydrochloride In a 500 mL 3-necked flask with a teflon paddle, a glass stir shaft, a water-cooled glass bearing, a dry nitrogen adapter and a septum with teflon-coated thermocouple, a solution of the crude ethyl (3R,4R,5S)-4-N-Acetyl(1,1-dimethylethyl)amino-5-N,N-diallylamino-3-(1-ethylpropoxy)-1-cyclohexene-1-carboxylate (49.54 g, 40.0 g at 81.6 wt %, 89.2 mmol) in 85 mL anhydrous ethanol is prepared at 250–300 rpm. Another solution of dry hydrogen chloride (3.86 g HCl, 106 mmol, 1.19 equiv) in 15 mL anhydrous ethanol is prepared separately at <25° C. and then added to the ethyl (3R,4R,5S)-4-N-Acetyl(1,1-dimethylethyl)amino-5-N,N-diallylamino-3-(1-ethylpropoxy)-1-cyclohexene-1-carboxylate solution in the flask at 20° C. over a few minutes. An additional 5 mL of ethanol are used to complete the transfer. The suspension is then cooled to 0–5° C.

105 mL of heptane are added dropwise over a few minutes and the suspension is cooled to −15° C. and then stirred for 1 h at 150 rpm. The precipitate is suction filtered, first washed with 15 mL of 1:1 ethanol-heptane at −15° C., then washed with 35 mL heptane at −5° C., before a final wash with 35 mL heptane at 25° C. The washed precipitate is then dried in vacuo (vacuum pump at 25° C. and ~1 mm Hg for 15 h) to yield 41.38 g of ethyl (3R,4R,5S)-4-N-Acetyl(1,1-dimethylethyl)amino-5-N,N-diallylamino-3-(1-ethylpropoxy)-1-cyclohexene-1-carboxylate hydrochloride (LC assay 97.9 wt % hydrochloride salt, Theoretical 43.3 g, 93.6% yield) as fluffy near-colorless crystals.

(e) Preparation of Ethyl (3R,4R,5S)-4-N-Acetylamino-5-N,N-diallylamino-3-(1-ethylpropoxy)-1-cyclohexene-1-carboxylate A 500 mL 3-necked round-bottomed flask equipped with an overhead (paddle) stirrer, a condenser with dry nitrogen adapter and a septum with thermocouple, is charged with 41.28 g (40.45 g, 83.4 mmol at 98.0 wt %) of the ethyl (3R,4R,5S)-4-N-Acetyl(1,1-dimethylethyl)amino-5-N,N-diallylamino-3-(1-ethylpropoxy)-1-cyclohexene-1-carboxylate hydrochloride as obtained from (d2). 70 mL of anhydrous ethanol are added to the flask before a solution of 3.20 g (87.8 mmol, 1.05 equivalent) dry hydrogen chloride in 10 mL anhydrous ethanol is added at 25–30° C. (teflon cannula). The suspension is heated at 62–63° C. (pot) (70° C. bath) for 3.5 h. 200 mL, of toluene (metal can) are added at 45° C. and the resulting solution distilled at atmospheric pressure under dry nitrogen until the pot temperature reaches 92° C. The solution is cooled to 0 to −5° C. and 35 mL of $H_2O$ added. A solution prepared by dissolving 4.81 g (120 mmol) of sodium hydroxide in 9.85 mL of $H_2O$ is then added portionwise at 0 to −5° C. until the pH of the aqueous layer is between 13 and 14 (10.79 g solution, 3.54 g NaOH, 97.1 mmol, 0.57 equiv required). The suspension is warmed to 20° C. and the layers separated. The aqueous layer is then extracted with 25 mL of toluene. The combined organic layers are concentrated in vacuo (rotary evaporator at 30–33° C. and 30–10 mm Hg) to yield 44.63 g of ethyl (3R,4R,5S)-4-N-Acetylamino-5-N,N-diallylamino-3-(1-ethylpropoxy)-1-cyclohexene-1-carboxylate (LC assay 68.7 wt %, Theoretical 32.73 g, 93.7% yield) as a yellow syrup with trace solids.

(f) Preparation of ethyl (3R,4R,5S)-4-N-Acetylamino-5-amino-3-(1-ethylpropoxy)-1-cyclohexene-1-carboxylate 31.78 g (0.08096 mol) of crude ethyl (3R,4R,5S)-4-N-Acetylamino-5-N,N-diallylamino-3-(1-ethylpropoxy)-1-cyclohexene-1-carboxylate, as prepared from (e), are dissolved in 77 mL of EtOH and charged to a 500 mL 3-necked round-bottomed jacketed flask equipped with an overhead (paddle) stirrer, a nitrogen inlet and a septum with thermocouple. 56 mL of Ethanol are used to rinse the transfer vessel to the reactor. 15.17 g of Dimethylbarbituric acid (0.09715 mol) are charged to the reactor flask followed by 0.8493 g of triphenylphosphine (0.003238 mol). A nitrogen sweep is placed on the reactor for 5 min and palladium acetate (0.1817 g, 0.0008096 mol) and ethanol (58 mL) are added and the jacket temperature set to 36° C. The reaction mixture is stirred for 2 h with agitation (284 RPM) under an atmosphere of nitrogen. The reaction is sampled for LC analysis and is completed. The jacket temperature is set to 10° C. for an overnight hold.

(g) Preparation of ethyl (3R,4R,5S)-4-N-Acetylamino-5-amino-3-(1-ethylpropoxy)-1-cyclohexene-1-carboxylate phosphate [1:1]

A 500 mL 3-necked round-bottomed jacketed flask equipped with an overhead (paddle) stirrer, an addition funnel with nitrogen inlet and a septum with thermocouple, is charged with a solution of 9.40 g (0.08153 mol) of 85% phosphoric acid, followed by 120 mL of absolute EtOH. The solution is heated to 52° C. The crude ethyl (3R,4R,5S)-4-N-Acetylamino-5-amino-3-(1-ethylpropoxy)-1-cyclohexene-1-carboxylate solution from (f) is warmed to 25° C., then approximately ⅔ of the solution is rapidly added to the crystallization vessel. The crystallization mixture is seeded with 102 mg of oseltamivir phosphate and crystallization occurs immediately. The slurry is aged 30 minutes before the remainder of the aminoacetamide solution is added over 30 minutes. The slurry is cooled to −18.8° C. (−20° C. jacket) over 15 h and aged 2 h. A 600 mL jacketed, fritted funnel with a $N_2$ sweep (set point of −17° C.) is used for the isolation. The slurry is poured into the funnel and as soon as the solvent front reaches the top of the cake, the crystallization vessel is rinsed with acetone (50 mL) and poured on top of the cake. The wet cake is washed with acetone (4×50 mL) followed by heptane (3×50 mL). The product is dried in vacuo (45° C. and ~20 mm Hg with a $N_2$ sweep for 18 h) to yield 29.86 g (89.9% yield) of ethyl (3R,4R,5S)-4-N-Acetylamino-5-amino-3-(1-ethylpropoxy)-1-cyclohexene-1-carboxylate phosphate [1:1] as a colorless solid.

EXAMPLE 3

Preparation of (3R,4R,5S)-5-amino-4-acetylamino-3-(1-ethyl-propoxy)-cyclohex-1-ene-carboxylic acid ethyl ester from (1S,5R,6R)-5-(1-ethyl-propoxy)-7-oxa-bicyclo[4.1.0]hept-3-ene-3-carboxylic acid ethyl ester.

a) Preparation of ethyl (3R,4S,5R)-5-N-(1,1-Dimethylethyl)amino-3-(1-ethylpropoxy)-4-hydroxy-cyclohexene-1-carboxylate A magnesium chloride-amine complex is first prepared by adding 65 mL (45.2 g, 0.619 mol, 1.50 equiv) of tert-butylamine to a suspension of 35.7 g (0.375 mol, 0.90 equiv) of magnesium chloride in 200 mL dry toluene at 25° C. The resulting colorless slurry is stirred at 25° C. for 6 h. A solution of 105.0 g (0.413 mol) of epoxide in 250 mL dry toluene is added via 18 gauge stainless steel cannula to the magnesium chloride-amine complex suspension at 20–25° C. The resulting suspension is heated at 50° C. for 8 h. More tert-butylamine (52 mL, 36.2 g, 0.495 mol, 1.20 equiv) is added and the solution heated for an additional 12 h. resulting in a yellow solution.

After cooling the yellow solution to 25° C., 200 mL of 10% w/w aqueous citric acid solution is added and the solution stirred at 25° C. for 30 min. The layers are then separated. The organic layer is concentrated in vacuo (rotary evaporator at 40° C. and 25 mm Hg then vacuum pump at 25° C. and 1 mm Hg for 17 h) to afford 135.3 g of orange oil (LC assay 96.0 wt %, 96.1% yield).

Steps (b), (c), (d), (e) and (f) are performed, as described supra, in Example 1.

What is claimed is:

1. A process for preparing 1,2-diamino compounds of formula

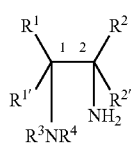

I and pharmaceutically acceptable addition salts thereof
wherein $R^1$, $R^{1'}$, $R^2$ and $R^{2'}$, independently from each other, are H, alkyl, alkenyl, alkynyl, cycloalkyl, cycloalkyl-lower alkyl, cycloalkyl-lower alkenyl, cycloalkyl-lower alkynyl, heterocyclyl, heterocyclyl-lower alkyl, heterocyclyl-lower alkenyl, heterocyclyl-lower alkynyl, aryl, aryl-lower alkyl, aryl-lower alkenyl, or aryl-lower alkynyl, or $R^1$ and $R^2$, $R^1$ and $R^{2'}$, $R^{1'}$ and $R^2$ or $R^{1'}$ and $R^{2'}$ taken together with the two carbon atoms to which they are bound, are a carbocyclic or heterocyclic ring system, or $R^1$ and $R^{1'}$ or $R^2$ and $R^{2'}$ taken together with the carbon atom to which they are bound, are a carbocyclic or heterocyclic ring system, wherein at least one of $R^1$, $R^{1'}$, $R^2$ and $R^{2'}$ is not H, and $R^3$ and $R^4$, are independently, a substituent of an amino group, wherein $R^3$ and $R^4$ are not both H, said process comprising the steps of:
a) reacting a 1,2-epoxide of formula

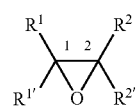

II wherein $R^1$, $R^{1'}$, $R^2$ and $R^{2'}$ are as above with an amine of formula $R^5NH_2$ wherein $R^5$ is a substituent of an amino group but not H,
to form a 2-aminoalcohol of formula

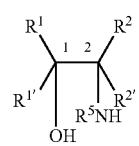

III wherein $R^1$, $R^{1'}$, $R^2$, $R^{2'}$ and $R^5$ are as above;
b) converting the 2-aminoalcohol of formula (III) to the aziridine of formula

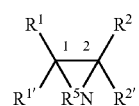

IV wherein $R^1$, $R^{1'}$, $R^2$, $R^{2'}$ and $R^5$ are as above;
c) reacting the aziridine of formula (IV) with an amine of formula $R^7NHR^8$, wherein $R^7$ and $R^8$, independently from each other, are a substituent of an amino group, to obtain a 1,2-diamino compound of formula

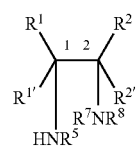

V wherein $R^1$, $R^{1'}$, $R^2$, $R^{2'}$, $R^5$, $R^7$ and $R^8$ are as above;
d) acylating the secondary amino group in position 1 of the 1,2-diamino compound of formula (V) to form an acylated 1,2-diamino compound of formula

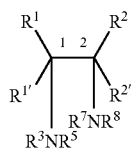

wherein $R^1$, $R^{1'}$, $R^2$, $R^{2'}$, $R^3$, $R^5$, $R^7$ and $R^8$ are as above;

e) removing $R^5$ from the acylated 1,2-diamino compound (VI) to produce an acylated 1,2-diamino compound of formula

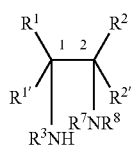

wherein $R^1$, $R^{1'}$, $R^2$, $R^{2'}$, $R^3$, $R^7$ and $R^8$ are as above; and f) deprotecting the amino group in position 2 of the 1,2-diamino compound of formula (VII) to produce the 1,2-diamino compound of formula (I).

2. The process of claim 1 wherein the 1, 2 epoxide is a cyclohexene oxide of formula

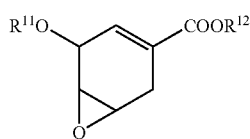

wherein $R^{11}$ and $R^{12}$ are as above.

3. The process of claim 2, wherein the cyclohexene oxide of formula (IX) is (1S,5R,6R)-5-(1-ethyl-propoxy)-7-oxa-bicyclo[4.1.0]hept-3-ene-3-carboxylic acid ethyl ester.

4. The process of claim 1 wherein the 1,2 diamino compound is a 4,5-diamino-shikimic acid derivative of formula

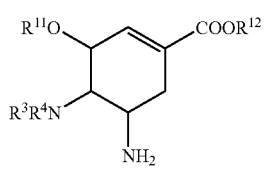

and pharmaceutically acceptable addition salts thereof, wherein $R^{11}$ is an alkyl group or a substituted alkyl group, $R^{12}$ is an alkyl group and $R^3$ and $R^4$ are, independently, H or a substituent of an amino group, wherein $R^3$ and $R^4$ are not both H.

5. The process of claim 4, wherein the 4,5-diamino-shikimic acid derivative of formula (VIII) is selected from the group consisting of ethyl (3R,4R,5S)-4-N-Acetylamino-5-amino-3-(1-ethylpropoxy)-1-cyclohexene-1-carboxylate, and ethyl (3R,4R,5S)-4-N-Acetylamino-5-amino-3-(1-ethylpropoxy)-1-cyclohexene-1-carboxylate phosphate (1:1).

6. The process of claim 1, wherein $R^5$ in the amine of formula $R^5NH_2$ is a straight chain or branched alkyl of 1 to 6 C-atoms.

7. The process of claim 6, wherein the amine of formula $R^5NH_2$ is tert-butylamine, 2-methylbutylamine, or 2-methylpentylamine.

8. The process of claim 7, wherein the amine of formula $R^5NH_2$ is tert-butylamine.

9. The process of claim 1, wherein the reaction of step a) is conducted in the presence of a catalyst.

10. The process of claim 9, wherein the catalyst is a metal catalyst or a magnesium halide catalyst or a magnesium halide derivative catalyst.

11. The process of claim 10, wherein the catalyst is a magnesium halide derivative.

12. The process of claim 10, wherein the catalyst is magnesium chloride.

13. The process of claim 1, wherein the cyclization in step (b) is performed in the presence of a sulfonylating agent.

14. The process of claim 1, wherein $R^7$ and $R^8$ in the amine of formula $R^7NHR^8$ are, independently, a straight chain or branched alkenyl of 2 to 6 C-atoms, benzyl, substituted benzyl or heterocyclyl methyl.

15. The process of claim 14, wherein the amine of $R^7NHR^8$ is a primary or secondary amine.

16. The process of claim 15, wherein the amine of $R^7NHR^8$ is a secondary amine.

17. The process of claim 16, wherein the amine of $R^7NHR^8$ is a diallylamine.

18. The process of claim 14, wherein the ring opening is performed in the presence of a catalyst.

19. The process of claim 18, wherein the catalyst is sulfonic acid or a derivative of sulfonic acid or a Lewis acid catalyst.

20. The process of claim 1, wherein the reaction in step (d) is carried out in the presence of acylating agents.

21. The process of claim 20, wherein the acylating agent is acetic anhydride.

22. The process of claim 1, wherein the reaction in step (d) is carried out in the presence of a catalyst.

23. The process of claim 22, wherein the catalyst is pyridine or a derivative of pyridine or an inorganic base.

24. The process of claim 22, wherein the catalyst is pyridine.

25. The process of claim 22, wherein the catalyst is an inorganic base.

26. The process of claim 22, wherein the catalyst is an organic base.

27. The process of claim 26, wherein the catalyst is sodium acetate.

28. The process of claim 1, wherein the reaction in step (d) is carried out at a temperature of from 70° C. to 120° C.

29. The process of claim 1, wherein the removal of the tert-butyl group from the acetamide of formula (VI) in step (e) is carried out by heating in acids.

30. The process of claim 1, wherein the cleavage of the tert-butyl group from the acetamide of formula (VI) is carried out with trifluoroacetic acid (TFA).

31. The process of claim 1, wherein the cleavage of the tert-butyl group from the acetamide of formula (VI) is carried out with hydrogen chloride in ethanol at reflux.

32. The process of claim 1, wherein the reaction in step (e) is carried out either with or without addition of any solvents.

33. The process of claim 1, wherein the conversion step (f) is performed at a temperature of from 20° C. to 70° C.

34. The process of claim 1, wherein the conversion step (f) is an alkenyl cleavage reaction performed in the presence of a metal catalyst wherein $R^7$ and $R^8$ are, independently, a straight chain or branched alkenyl of 2 to 6 C-atoms.

35. The process of claim 34, wherein the catalyst is palladium acetate.

36. The process of claim 34, wherein the catalyst is tetrakis(triphenylphosphine) palladium.

37. A process for preparing an acylated 1,2-diamino compound of formula

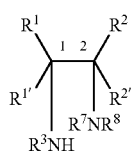

VII wherein $R^1$, $R^{1'}$, $R^2$ and $R^{2'}$, independently from each other, are H, alkyl, alkenyl, alkynyl, cycloalkyl, cycloalkyl-lower alkyl, cycloalkyl-lower alkenyl, cycloalkyl-lower alkynyl, heterocyclyl, heterocyclyl-lower alkyl, heterocyclyl-lower alkenyl, heterocyclyl-lower alkynyl, aryl, aryl-lower alkyl, aryl-lower alkenyl, or aryl-lower alkynyl, or $R^1$ and $R^2$, $R^1$ and $R^{2'}$, $R^{1'}$ and $R^2$ or $R^{1'}$ and $R^2$ taken together with the two carbon atoms to which they are bound, are a carbocyclic or heterocyclic ring system, or $R^1$ and $R^{1'}$ or $R^2$ and $R^{2'}$ taken together with the carbon atom to which they are bound, are a carbocyclic or heterocyclic ring system, wherein at least one of $R^1$, $R^{1'}$, $R^2$ and $R^{2'}$ is not H, and $R^3$ is a substituent of an amino group and not H $R^7$ and $R^8$, independently from each other, are H or a substituent of an amino group, wherein $R^7$ and $R^8$ are not both H comprising removing the alkyl group from position 1 of the acylated 1,2-diamino compound of formula (VI)

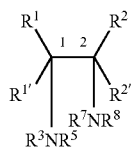

VI wherein $R^1$, $R^{1'}$, $R^2$, $R^{2'}$, $R^3$, $R^5$, $R^7$ and $R^8$ are as above.

38. The process of claim 37, wherein $R^5$ is a tert-butyl group.

39. A compound of the formula

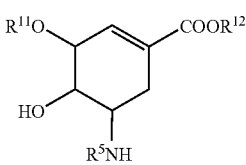

X wherein $R^{11}$ is an alkyl group or substituted alkyl group and $R^5$ and $R^{12}$ are independently, an alkyl group and pharmaceutically acceptable addition salts thereof.

40. The compound of claim 39, wherein the compound is ethyl (3R,4S,5R)-5-N-(1,1-Dimethylethyl)amino-3-(1-ethylpropoxy)-4-hydroxy-cyclohexene-1-carboxylate.

41. A compound of the formula

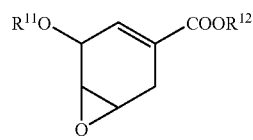

IX wherein $R^{11}$ is an alkyl group or substituted alkyl group and $R^5$ and $R^{12}$ are independently, an alkyl group and pharmaceutically acceptable addition salts thereof.

42. The compound of claim 41 wherein the compound is ethyl (3R,4S,5R)-4,5-(1,1-Dimethylethyl)imino-3-(1-ethylpropoxy)-1-cyclohexene-1-carboxylate.

43. A compound of the formula

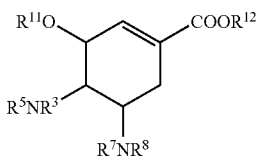

XII wherein $R^{11}$ is an alkyl group, substituted alkyl group and $R^{12}$ is an alkyl group, $R^3$ is a substituent of an amino group, $R^5$ is an alkyl group, and $R^7$ and $R^8$ are, independently, H or a substituent of an amino group, wherein $R^7$ and $R^8$ are not both H, and pharmaceutically acceptable addition salts thereof.

44. The compound of claim 43, wherein the compound is ethyl (3R,4R,5S)-5-N,N-Diallylamino-4-(1,1-dimethylethyl)amino-3-(1-ethylpropoxy)-1-cyclohexene-1-carboxylate.

45. The compound of claim 43, wherein the compound is ethyl (3R,4R,5S)-4-N-Acetyl(1,1-dimethylethyl)amino-5-N,N-diallylamino-3-(1-ethylpropoxy)-1-cyclohexene-1-carboxylate.

46. The compound of claim 43, wherein the compound is ethyl (3R,4R,5S)-4-N-Acetyl(1,1-dimethylethyl)amino-5-N,N-diallylamino-3-(1-ethylpropoxy)-1-cyclohexene-1-carboxylate hydrochloride.

47. The process of claim 1, wherein the step a) of reacting the 1,2-epoxide occurs by pre-mixing the amine with a catalyst to form an amine-catalyst complex before mixing the complex with the 1,2-epoxide.

* * * * *